(12) United States Patent
Yoon et al.

(10) Patent No.: US 8,437,862 B2
(45) Date of Patent: May 7, 2013

(54) MAGNETIC FIELD DETECTION USING MAGNETOHYDRODYNAMIC EFFECT

(75) Inventors: Hyun J. Yoon, Vadnais Heights, MN (US); Ben W. Herberg, Andover, MN (US); Michael L. Ellingson, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 143 days.

(21) Appl. No.: 13/074,143

(22) Filed: Mar. 29, 2011

(65) Prior Publication Data

US 2012/0253425 A1 Oct. 4, 2012

(51) Int. Cl.
A61N 1/00 (2006.01)
(52) U.S. Cl.
USPC ............................................. 607/63; 607/27
(58) Field of Classification Search ............... 607/4–28, 607/62, 63
See application file for complete search history.

(56) References Cited

U.S. PATENT DOCUMENTS

| | | | |
|---|---|---|---|
| 5,697,958 A | 12/1997 | Paul et al. | |
| 5,766,227 A * | 6/1998 | Nappholz et al. | 607/9 |
| 6,073,039 A | 6/2000 | Berson | |
| 6,440,059 B1 | 8/2002 | Haas et al. | |
| 7,303,581 B2 | 12/2007 | Peralta | |
| 7,572,231 B2 | 8/2009 | Pearlman | |
| 2007/0167737 A1 | 7/2007 | Frank et al. | |
| 2007/0276445 A1 | 11/2007 | Sanghera et al. | |
| 2008/0082012 A1 | 4/2008 | Gunderson | |
| 2008/0114237 A1 | 5/2008 | Demharter et al. | |
| 2008/0154116 A1 | 6/2008 | Duensing et al. | |

FOREIGN PATENT DOCUMENTS

| | | |
|---|---|---|
| WO | 9829030 | 7/1998 |
| WO | 9923942 | 5/1999 |
| WO | 01/13997 A1 | 3/2001 |
| WO | 0137726 | 5/2001 |
| WO | 2006/060587 A1 | 6/2006 |
| WO | 2007/127705 A1 | 11/2007 |
| WO | 2010008833 | 1/2010 |

OTHER PUBLICATIONS

Kangarlu et al., "Biological Effects and Health Implications in Magnetic Resonance Imaging", Concepts in Magnetic Resonance., vol. 12(5), 2000, pp. 321-359.
Nijm et al., "Characterization of the Magnetohydrodynamic Effect as a Signal from the Surface Electrocardiogram during Cardiac Magnetic Resonance Imaging", Computers in Cardiology, 2006, vol. 33, pp. 269-272.

(Continued)

Primary Examiner — Scott Getzow
(74) Attorney, Agent, or Firm — Stephen W. Bauer; Michael J. Ostrom

(57) ABSTRACT

An IMD may transition to an MRI mode automatically in response to detecting one or more conditions indicative of the presence of a strong magnetic field. Large static magnetic fields, such as those produced by an MRI device, may interact with the blood of a patient as it flows through the magnetic field to produce a voltage, a phenomenon referred to as the magnetohydrodynamic (MHD) effect. The voltage produced by the MHD effect is proportional to the strength of the magnetic field. As such, the voltage produced by blood flow in the strong magnetic field of an MRI device may result in a change in a characteristic of an electrogram (EGM). The IMD may detect the change in the characteristic of the EGM caused by the MHD effect and transition to operation in the MRI mode in response to at least the change in the EGM.

19 Claims, 7 Drawing Sheets

OTHER PUBLICATIONS

Price, "The AAPM/RSNA Physics Tutorial for Residents: MR Imaging Safety Considerations", Radiographics, 1999, vol. 19, pp. 1641-1651.

Gimbel, "Unexpected Pacing Inhibition Upon Exposure to the 3T Static Magnetic Field Prior to Imaging Acquisition: What is the Mechanism?", Heart Rhythm Society, 2011, pp. 944-945.

(PCT/US2012/020253) PCT Notification of Transmittal of the International Search Report and the Written Opinion of the International Searching Authority.

Tenforde et al; "Magnetically Induced Electric Fields and Currents in the Circulatory System," Progress in Biophysics and Molecular Biology, Pergamon Press, Oxford, GB, vol. 87, pp. 2-3.

* cited by examiner

MAGNETIC FIELD DETECTION USING MAGNETOHYDRODYNAMIC EFFECT

TECHNICAL FIELD

This disclosure relates generally to implantable medical systems. In particular, this disclosure describes techniques for detecting magnetic resonance imaging (MRI) devices using the magnetohydrodynamic effect.

BACKGROUND

A wide variety of implantable medical systems that deliver a therapy or monitor a physiologic condition of a patient have been clinically implanted or proposed for clinical implantation in patients. The implantable medical system may include an implantable medical lead connected to an implantable medical device (IMD). For example, implantable leads are commonly connected to implantable pacemakers, defibrillators, cardioverters, or the like, to form an implantable cardiac system that provides electrical stimulation to the heart or sensing of electrical activity of the heart. The electrical stimulation pulses can be delivered to the heart and the sensed electrical signals can be sensed by electrodes disposed on the leads, e.g., typically near distal ends of the leads. Implantable leads are also used in neurological devices, muscular stimulation therapy, gastric system stimulators and other implantable medical devices (IMDs).

Patients that have implantable medical systems may benefit, or even require, various medical imaging procedures to obtain images of internal structures of the patient. One common medical imaging procedure is magnetic resonance imaging (MRI). MRI procedures may generate higher resolution and/or better contrast images (particularly of soft tissues) than other medical imaging techniques. MRI procedures also generate these images without delivering ionizing radiation to the body of the patient, and, as a result, MRI procedures may be repeated without exposing the patient to such radiation.

During an MRI procedure, the patient or a particular part of the patient's body is positioned within an MRI device. The MRI device generates a variety of magnetic and electromagnetic fields to obtain the images of the patient, including a static magnetic field, gradient magnetic fields, and radio frequency (RF) fields. The static magnetic field may be generated by a primary magnet within the MRI device and may be present prior to initiation of the MRI procedure. The gradient magnetic fields may be generated by electromagnets of the MRI device and may be present during the MRI procedure. The RF fields may be generated by transmitting/receiving coils of the MRI device and may be present during the MRI procedure. If the patient undergoing the MRI procedure has an implantable medical system, the various fields produced by the MRI device may have an effect on the operation of the medical leads and/or the IMD to which the leads are coupled. For example, the gradient magnetic fields or the RF fields generated during the MRI procedure may induce energy on the implantable leads (e.g., in the form of a current), which may cause oversensing by the IMD.

SUMMARY

The IMD may transition from operation in a normal mode to another mode in the presence of a magnetic field to reduce the likelihood of interference. The IMD may transition from the normal mode to an MRI mode in response to detecting presence of a large static magnetic field associated with an MRI device. As described in detail herein, the IMD may detect the presence of the magnetic field by analyzing an electrogram (EGM). Blood flow through a magnetic field may produce a voltage, a phenomenon referred to as the magnetohydrodynamic (MHD) effect. The voltage produced by the MHD effect has a linear relationship with the strength of the magnetic field. As such, a strong magnetic field may result in a change in a characteristic of the EGM, such as a change in a T-wave or an S-T segment of the EGM. Upon identifying such a change, the IMD may transition to the MRI mode.

In addition to transitioning from the normal mode to the MRI mode in response to detecting a strong magnetic field, the IMD may transition from the normal mode to a "magnet mode" in response to detecting magnetic fields of a smaller strength. For example, the IMD may transition to the magnet mode in response to detecting the presence of a magnetic field of a handheld magnet, such as a telemetry head magnet or a patient magnet. The strength of such a magnetic field is typically much smaller than the strength of the magnetic fields associated with MRI devices. As such, the handheld magnet typically does not produce much of an MHD effect. The IMD may therefore use the change in the EGM caused by the MHD effect to differentiate a magnetic field generated by a handheld magnet or other smaller strength magnet from a static magnetic field of an MRI device.

For example, the IMD may have a single threshold magnetic field sensor that determines the presence of a magnetic field having a strength that exceeds a threshold (e.g., 1 mT). In this case, IMD 22 is unable to determine whether the magnetic field is associated with an MRI device or other magnet, such as the handheld magnet. However, the IMD monitors for a change in the EGM due the MHD effect and transitions to the magnet mode when no change in the EGM is identified and transitions to the MRI mode when the change in the EGM is identified. In this manner, the change in the EGM due to the MHD effect may be used to differentiate magnetic fields of different strengths.

In one example, this disclosure is directed to a method comprising identifying a change in a characteristic of an electrogram (EGM) measured by an implantable medical device indicative of the presence of a magnetic field determining a magnitude of the change in the characteristic of the EGM, and adjusting operation of the implantable medical device based on the magnitude of the change in the characteristic of the EGM.

In another example, this disclosure is directed to an implantable medical system comprising at least one implantable medical lead that includes at least one electrode and an implantable medical device connected to the medical lead, the implantable medical device comprising a control module configured to identify a change in a characteristic of an electrogram (EGM) indicative of the presence of a magnetic field, determine a magnitude of the change in the characteristic of the EGM, and adjust operation of the implantable medical device based on the magnitude of the change in the characteristic of the EGM.

In a further example, this disclosure is directed to a computer-readable medium comprising instructions that, when executed, cause an implantable medical device to identify a change in a characteristic of an electrogram (EGM) indicative of the presence of magnetic field, determine a magnitude of the change in the characteristic of the EGM, and adjust operation of the implantable medical device based on the magnitude of the change in the characteristic of the EGM.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
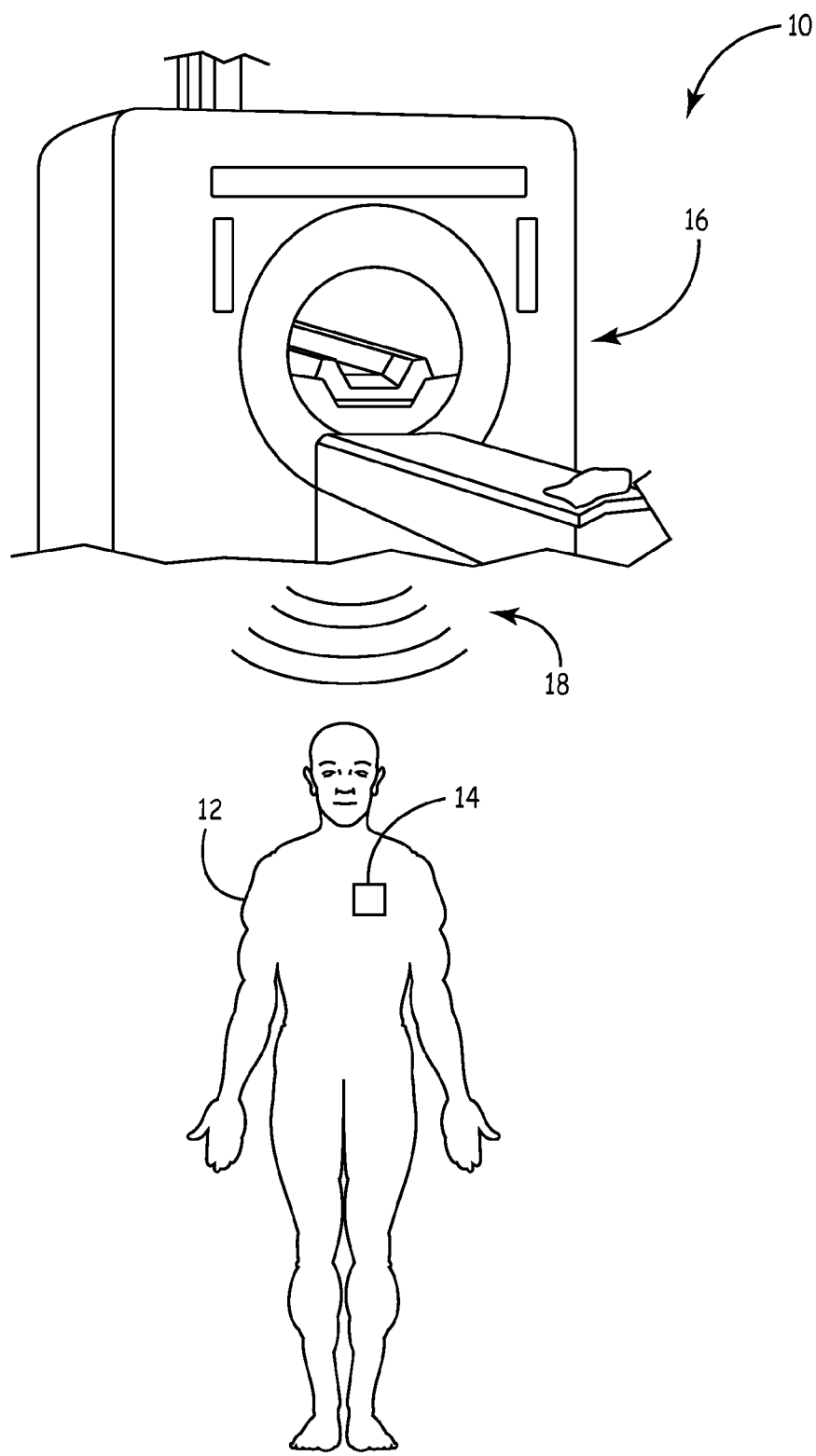
FIG. 1 is a conceptual diagram illustrating an environment in which a patient with an implantable medical system is exposed to external fields.

FIG. 1 is a conceptual diagram illustrating an environment 10 in which a patient 12 with an implantable medical system 14 is exposed to an external field 18. In the example illustrated in FIG. 1, environment 10 includes an MRI device 16 that generates external field 18. MRI device 16 generates magnetic and RF fields to produce images of body structures for diagnosing injuries, diseases and/or disorders. In particular, MRI device 16 generates a static magnetic field, gradient magnetic fields and RF fields as is well known in the art. The static magnetic field is a large non time-varying magnetic field that is typically always present around MRI device 16 whether or not an MRI procedure is in progress. Gradient magnetic fields are pulsed magnetic fields that are typically only present while the MRI procedure is in progress. RF fields are pulsed high frequency fields that are also typically only present while the MRI procedure is in progress.

The magnitude, frequency or other characteristic of the static magnetic field, gradient magnetic fields and RF fields may vary based on the type of MRI device producing the field or the type of MRI procedure being performed. A 1.5 T MRI device, for example, will produce a static magnetic field of about 1.5 Tesla (T) and have a corresponding RF frequency of about 64 megahertz (MHz) while a 3.0 T MRI device will produce a static magnetic field of about 3.0 Tesla and have a corresponding RF frequency of about 128 MHz. However, other MRI devices may generate different fields.

Implantable medical system 14 may, in one example, include an IMD connected to one or more leads. The IMD may be an implantable cardiac device that senses electrical activity of a heart of patient 12 and/or provides electrical stimulation therapy to the heart of patient 12. For example, the IMD may be an implantable pacemaker, implantable cardioverter defibrillator (ICD), cardiac resynchronization therapy defibrillator (CRT-D), cardioverter device, or combinations thereof. The IMD may alternatively be a non-cardiac implantable device, such as an implantable neurostimulator or other device that provides electrical stimulation therapy.

Some or all of the various types of fields produced by MRI device 16 (which are represented by external field 18) may have undesirable effects on implantable medical system 14. In one example, the gradient magnetic fields and/or the RF fields generated during the MRI procedure may induce enemy on the conductors of the leads (e.g., in the form of a current). The induced energy on the leads may be conducted to the IMD and inappropriately detected as physiological signals, a phenomenon often referred to as oversensing. The detection of the induced energy on the leads as physiological signals may result in the IMD delivering therapy when it is not desired (e.g., triggering a pacing pulse) or withholding therapy when it is desired (e.g., inhibiting a pacing pulse).

The IMD may be configured to operate in an "MRI mode" upon detecting the presence of MRI device 16. Operation of the IMD in the "MRI mode" may refer to an operating state of the IMD in which the undesirable effects (e.g., oversensing) that may be caused by the gradient magnetic fields and RF fields of MRI device 16 are reduced, and possibly eliminated. When operating in the MRI mode, the IMD is configured to operate with different functionality compared to the "normal mode" of operation. In one example, the IMD may operate in either a non-pacing mode (e.g., sensing only mode) or in an asynchronous pacing mode as the MRI mode. The IMD may also turn off high voltage therapy (e.g., defibrillation therapy) while operating in the MRI mode. The IMD may also turn off telemetry functionality, e.g., wakeup or other telemetry activity, during operation in the MRI mode. Other adjustments may be made as described herein. In this manner, patient 12 having implanted medical system 14 may receive an MRI procedure that exposes implantable medical system 14 to external fields, such as external field 18 of FIG. 1, with a reduced likelihood of interference with operation of the IMD.

The IMD may transition to the MRI mode automatically in response to detecting one or more conditions indicative of the presence of MRI device 16. Large static magnetic fields, such as those produced by MRI device 16, may interact with the blood of patient 12 as it flows through the magnetic field. In particular, the blood flow through the large static magnetic field of MRI device 16 may produce a voltage, a phenomenon referred to as the magnetohydrodynamic (MHD) effect. The voltages produced by the MHD effect may result in a change in a characteristic of an electrogram (EGM) detected by the IMD. In this manner, the change in the characteristic of the EGM is indicative of the presence of a large static magnetic field. As will be described in detail herein, the IMD may detect the change in the characteristic of the EGM due to the MHD effect and transition to operation in the MRI mode in response to the detection. In other examples, the IMD may monitor for the MHD effect in conjunction with other criteria indicative of a magnetic field.

After the MRI procedure is complete, the IMD may transition back to the normal mode of operation, e.g., turn high voltage therapy back on and/or have pacing that is triggered and/or inhibited as a function of sensed signals. The IMD may automatically revert to the normal mode of operation in response to no longer detecting the MHD effect on the EGM no longer detecting another condition indicative of presence of the magnetic field, after expiration of a timer or a combination thereof. Alternatively, the IMD may be manually programmed into the normal mode of operation via a command received from an external device, such as programming device.

Figure 2:
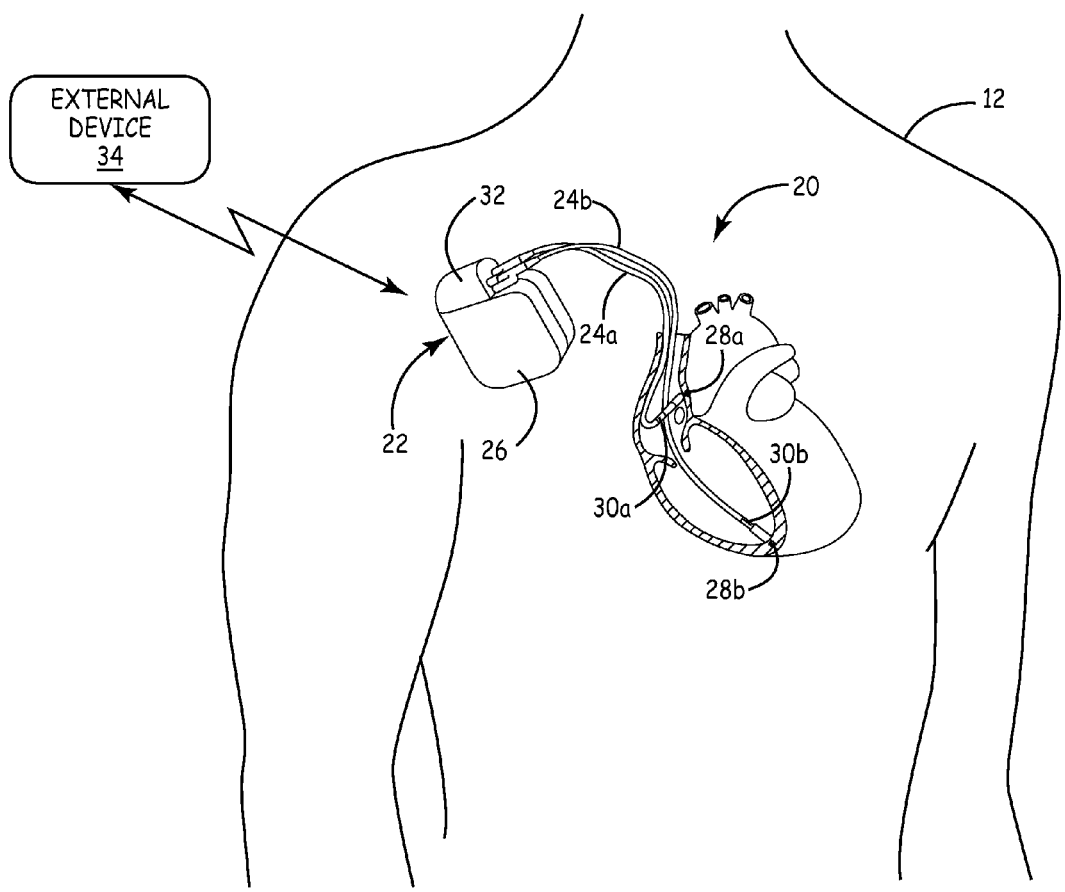
FIG. 2 is a conceptual diagram illustrating an example implantable medical system.

FIG. 2 is a conceptual diagram illustrating an example implantable medical system 20. Implantable medical system 20 may correspond with implantable medical system 14 of FIG. 1. Implantable medical system 20 includes an IMD 22 connected to leads 24a,b. IMD 22 includes a housing 26 within which electrical components and a power source of IMD 22 are housed. Housing 26 can be formed from conductive materials, non-conductive materials or a combination thereof. As will be described in further detail herein, housing 26 may house one or more processors, memories, transmitters, receivers, sensors, sensing circuitry, therapy circuitry and other appropriate components.

Leads 24a,b each includes one or more electrodes. In the example illustrated in FIG. 2, leads 24a,b each include a respective tip electrode 28a,b and ring electrode 30a,b located near a distal end of their respective leads 24a,b. When implanted, tip electrodes 28a,b and/or ring electrodes 30a,b are placed relative to or in a selected tissue, muscle, nerve or other location within the patient 12. In the example illustrated in FIG. 2, tip electrodes 28a,b are extendable helically shaped electrodes to facilitate fixation of the distal end of leads 24a,b to the target location within patient 12. In this manner, tip electrodes 28a,b are formed to define a fixation mechanism. In other embodiments, one or both of tip electrodes 28a,b may be formed to define fixation mechanisms of other structures. In other instances, leads 24a,b may include a fixation mechanism separate from tip electrode 28a,b. Fixation mechanisms can be any appropriate type, including a grapple mechanism, a helical or screw mechanism, a drug-coated connection mechanism in which the drug(s) serves to reduce infection and/or swelling of the tissue, or other attachment mechanism.

Leads 24a,b are connected at a proximal end to IMD 22 via connector block 32. Connector block 32 may include one or more receptacles that interconnect with one or more connector terminals located on the proximal end of leads 24a,b. Leads 24a,b are ultimately electrically connected to one or more of the electrical components within housing 26.

One or more conductors (not shown in FIG. 2) extend within leads 24a,b from connector block 32 along the length of the lead to engage the ring electrode 30a,b and tip electrode 28a,b, respectively. In this manner, each of tip electrodes 28a,b and ring electrodes 30a,b is electrically coupled to a respective conductor within its associated lead bodies. For example, a first electrical conductor can extend along the length of the body of lead 24a from connector block 32 and electrically couple to tip electrode 28a and a second electrical conductor can extend along the length of the body of lead 24a from connector block 32 and electrically couple to ring electrode 30a. The respective conductors may electrically couple to circuitry, such as a therapy module or a sensing module, of IMD 22 via connections in connector block 32. The electrical conductors transmit therapy from the therapy module within IMD 22 to one or more of electrodes 28a,b and 30a,b and transmit sensed electrical signals from one or more of electrodes 28a,b and 30a,b to the sensing module within IMD 22.

As will be described in further detail herein, IMD 22 may transition from operation in a "normal mode" to another mode in the presence of a magnetic field. Operation of IMD 22 in the normal mode may describe a typical operating state of the IMD. The typical operating state may involve operation of ordinary therapy and/or sensing modes in the IMD to provide optimal therapy to patient 12. In the case of an IMD functioning as an implantable cardioverter-defibrillator, for example, the normal mode may permit normal sensing to support normal pacing, cardioversion and/or defibrillation therapy functions.

IMD 22 may transition from the normal mode to the MRI mode in response to detecting a static magnetic field generated by MRI device 16. As described in detail herein, IMD 22 may detect a change in the characteristic of the EGM due to the MHD effect and adjust operation of IMD 22 in response to the detection. IMD 22 may monitor for the MHD effect in conjunction with other factors indicative of a magnetic field to detect presence of MRI device 16.

In addition to transitioning from the normal mode to the MRI mode in response to detecting a strong magnetic field, the IMD may transition from the normal mode to a "magnet mode" in response to detecting magnetic fields of a smaller strength than the magnetic fields associated with MRI device 16. In the magnet mode, IMD 22 may operate with different functionality than the normal mode and the MRI mode. IMD 22 may adjust therapy or sensing operations of IMD 22 during operation in the magnet mode, such as transitioning to an asynchronous pacing mode and/or turning off high voltage therapy (e.g., defibrillation therapy). The magnet mode is typically permanently configured by the manufacturer. In other words, the operational parameters of the magnet mode (e.g., the pacing mode, pacing rate, pacing pulse amplitude or other characteristic) are not configurable by a physician, technician, clinician or other user. To the contrary, the MRI mode is configurable such that it may be adjusted on a patient-by-patient basis. IMD 22 may also, in some instances, activate telemetry circuitry within IMD 22 to initiate communication, e.g., transfer of data, between IMD 22 and external device 34. IMD 22 may, for example, wake up or otherwise power on the telemetry circuitry of IMD 22 to monitor for a communication from external device 34 or transmit a communication to external device 34 in response to detecting the small magnetic field of the handheld magnet.

As indicated above, IMD 22 may transition to different operating modes in response to detecting different magnetic fields, e.g., to the MRI mode in response to detecting the static magnetic field associated with MRI device 16 and to the magnet mode in response to detecting the magnetic field having a smaller strength, such as that associated with a handheld magnet. As such, it is desirable that IMD 22 be able to accurately differentiate between magnetic fields having different strengths. The strength of the static magnetic field associated with MRI device 16 is typically much larger than the strength of the handheld magnet or other magnetic fields the patient encounters. As described above, MRI device 16 may have a static magnetic field that is larger than approximately 1.0 Tesla. The strength of the handheld magnet, however, is typically in the millitesla (mT) range. For example, a handheld magnet may have a strength in the range of approximately 10 mT to 100 mT.

However, the magnetic field sensors of IMD 22 may not always be capable of differentiating the strengths of the magnetic fields. For example, the magnetic field sensors may only be capable of determining that the magnetic field exceeds a threshold (e.g., 1 mT). In this case, IMD 22 is unable to determine whether the magnetic field is from a handheld magnet or a static magnetic field associated with MRI device 16. One technique to differentiate the magnetic field of a handheld magnet from the magnetic field associated with MRI device 16 is to monitor for a change in a characteristic of the EGM due to the MHD effect. Because the handheld magnet generates a magnetic field having a small strength (e.g., 10-100 mT) and small area (e.g., only in the vicinity of IMD 22), there is little, if any, change to the EGM due to the MHD effect. However, the magnetic field generated by MRI device 16 is much larger in strength greater than 1.0 T) and applied to a much larger area of patient 12 (e.g., an entire section of the body), thereby creating a noticeable change to the EGM due to the MHD effect. As such, monitoring for a change in the EGM due the MHD effect alone or in combination with a magnetic field sensor, or other sensor, provides an effective way to differentiate magnetic fields of varying strengths. In fact, in some instances, IMD 22 may be capable of distinguishing between various types of MRI devices 16 based on the magnitude of the change to the EGM caused by the MHD effect.

IMD 22 may transition back to the normal operating mode after the MRI procedure or communication session has ended. IMD 22 may automatically revert to the normal operating mode in response to no longer detecting the magnetic field, whether it was generated by a handheld magnet, MRI device 16 or other source, after expiration of a timer or a combination thereof. Alternatively, IMD 22 may be manually programmed into the normal operating mode via a command received from an external device 34.

IMD 22 may communicate with external device 34 to exchange data with external device 34. External device 34 may, for example, communicate with IMD 22 to provide the command to transition to the normal operating mode. As another example, IMD 22 may receive one more operating parameters for operation of IMD 22 from external device 34. The operating parameters may be associated with the MRI mode of operation that is utilized in response to detecting the static magnetic field associated with MRI device 16. IMD 22 may also transmit sensed physiological data, diagnostic determinations made based on the sensed physiological data, IMD performance data and/or IMD integrity data to external device 34. IMD 22 and external device 34 may communicate via wireless communication using any techniques known in the art. Examples of communication techniques may include, for example, low frequency or RF telemetry, although other techniques are also contemplated.

External device 34 may, in some instances, include a telemetry head that extends from external device 34 and is placed in close proximity to the implant site of IMD 22 to initiate and perform communication with IMD 22. In one example, the telemetry head may include a telemetry head magnet that generates a magnetic field ("telemetry head field") and an antenna (not shown) that transmits and receives communications with IMD 22. As such, the handheld magnet may be the telemetry head magnet in some examples.

The configuration of implantable medical system 20 illustrated in FIG. 2 is merely an example. In other examples, implantable medical system 20 may include more or fewer leads extending from IMD 22. For example, IMD 22 may be coupled to three leads, e.g., a third lead implanted within a left ventricle of the heart of the patient. In another example, IMD 22 may be coupled to a single lead that is implanted within either an atrium or ventricle of the heart of the patient. As such, IMD 22 may be used for single chamber or multi-chamber cardiac rhythm management therapy.

In addition to more or fewer leads, each of the leads may include more or fewer electrodes. In instances in which IMD 22 is used for therapy other than pacing, e.g., defibrillation or cardioversion, the leads may include elongated electrodes, which may, in some instances, take the form of a coil. IMD 22 may deliver defibrillation or cardioversion shocks to the heart via any combination of the elongated electrodes and housing electrode. As another example, medical system 20 may include leads with a plurality of ring electrodes, e.g., as used in some implantable neurostimulators, without a tip electrode or with one of the ring electrodes functioning as the "tip electrode."

Figure 3:
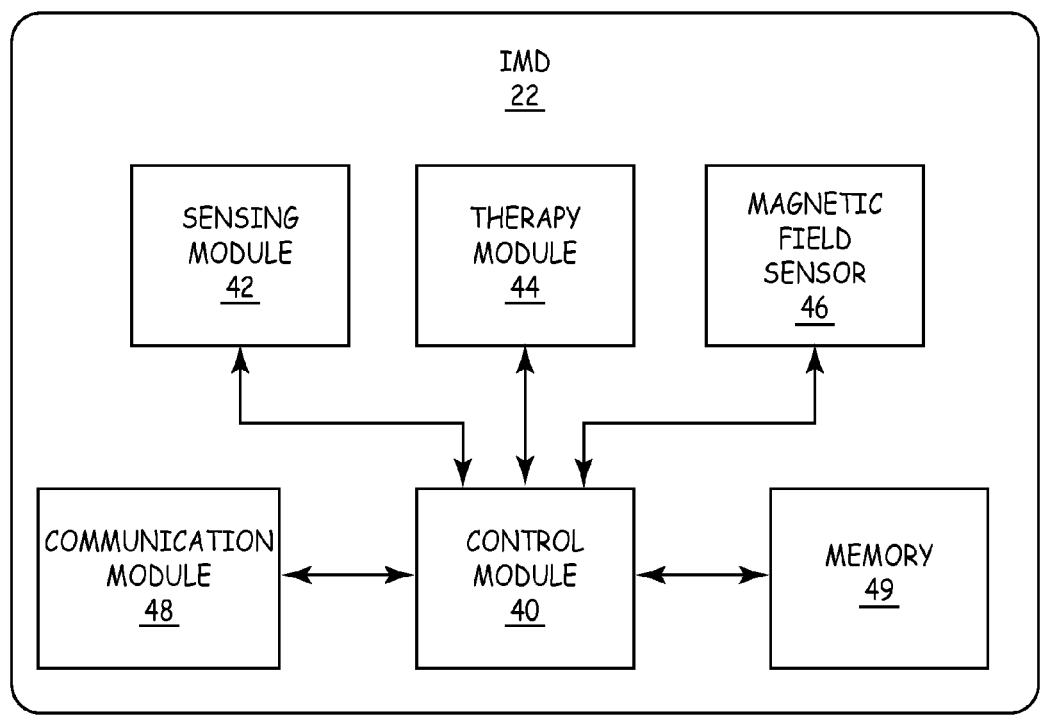
FIG. 3 is a functional block diagram of an example configuration of electronic components of an implantable medical device.

FIG. 3 is a functional block diagram of an example configuration of electronic components of IMD 22. IMD 22 includes a control module 40, sensing module 42, therapy module 44, magnetic field sensor 46, communication module 48 and memory 49. The electronic components may receive power from a power source (not shown in FIG. 3). In other examples, IMD 22 may include more or fewer electronic components. In addition, any of the described modules or components may be implemented together on a common hardware component or separately as discrete but interoperable hardware or software components. Depiction of different features as modules or components is intended to highlight different functional aspects and does not necessarily imply that such modules or units must be realized by separate hardware or software components. Rather, functionality associated with one or more modules may be performed by separate hardware or software components, or integrated within common or separate hardware or software components.

Memory 49 may include computer-readable instructions that, when executed, cause IMD 22 and/or control module 40 to perform various functions attributed to IMD 22 and control module 40 in this disclosure. In other words, memory 49 includes computer-readable instructions that control operation of IMD 22. Memory 49 may, for example, store operating parameters for any of a number of operating modes, including at least the normal mode, the magnet mode and one or more MRI modes. Memory 49 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media, or combination thereof.

Control module 40 may include any one or more of a microprocessor, a controller, a digital signal processor (DSP), an application specific integrated circuit (ASIC), a field-programmable gate array (FPGA), or equivalent discrete or integrated circuitry, including analog circuitry, digital circuitry, or logic circuitry. In some examples, control module 40 may include multiple components, such as any combination of one or more microprocessors, one or more controllers, one or more DSPs, one or more ASICs, or one or more FPGAs, as well as other discrete or integrated logic circuitry. The functions attributed, to control module 40 herein may be embodied as software, firmware, hardware or any combination thereof.

Control module 40 may communicate with sensing module 42 and therapy module 44 to operate IMD in the selected operating mode. Sensing module 42 and therapy module 44 are electrically coupled to some or all of electrodes 28a,b and 30a,b via the conductors of leads 24a,b. Sensing module 42 is configured to obtain signals from leads 24a,b. Control module 40 may process the signals from leads 24a,b to monitor electrical activity of the heart of patient 12. Control module 40 may, for example, generate EGM waveforms based on the signals received from sensing module 42. Control module 40 may also generate marker channel data based on the detected cardiac activity. For example, marker channel data may include data that indicates the occurrence and timing of sensing, diagnosis, and therapy events associated with patient 12 and/or IMD 22.

Control module 40 may store EGM waveforms and marker channel data in memory 49. Control module 40 may analyze the EGM waveforms and/or marker channel data to detect cardiac events (e.g., tachyarrhythmias). Control module 40 may also analyze the EGM waveforms to detect changes in the characteristics of the EGM indicative of the presence of a strong magnetic field as will be described in further detail herein. Control module 40 may also later retrieve stored EGMs from memory 49, e.g., upon a request from external device 34 received via communication module 48. In further examples, sensing module 42 is coupled to one or more sensors that are not included on leads 24a,b, via a wired or wireless coupling. Such sensors may include pressure sensors, accelerometers, flow sensors, blood chemistry sensors, activity sensors or other types of physiological sensors. One such sensor is magnetic field sensor 46 within IMD 22. Signals monitored by sensing module 42 may be stored in memory 49.

Therapy module 44 is configured to generate and deliver electrical stimulation therapy to the heart. Control module 40 may control therapy module 44 to deliver electrical stimulation therapy to the heart according to one or more therapy programs, which may be stored in memory 49. Control module 40 may, in some instances, control therapy module 44 to deliver therapy to patient 12 as a function of the signals sensed by sensing module 42. For example, control module 40 may control therapy module 44 to trigger and/or inhibit pacing pulses to the heart as a function of the sensed signals received from sensing module 42. In other instances, control module 40 may control therapy module 44 to deliver therapy to patient 12 without regard to signals sensed by sensing module 42, such as in an asynchronous pacing mode.

Therapy module 44 may, under the control of control module 40, also be configured to generate and deliver cardioversion and defibrillation therapy to the heart. For example, in the event that control module 40 detects an atrial or ventricular tachyarrhythmia, control module 40 may load an ATP regimen from memory 49, and control therapy module 44 to implement the ATP regimen. Therapy module 44 may also include a high voltage charge circuit and a high voltage output circuit that generate high voltage shocks to defibrillate the heart.

Communication module 48 includes any suitable hardware, firmware, software or any combination thereof for communicating with another device, such as external device 34 and/or a patient monitor, e.g., by wireless telemetry. For example, communication module 48 may include appropriate modulation, demodulation, frequency conversion, filtering, and amplifier components for transmission and reception of data. Under the control of control module 40, communication module 48 may receive downlink telemetry from and send uplink telemetry to external device 34 with the aid of an antenna (not shown) in IMD 22. Control module 40 may provide the data to be uplinked to external device 34 and the control signals for a telemetry circuitry within communication module 48, e.g., via an address/data bus.

IMD 22 may transition from operation in a normal mode to another mode, e.g., MRI mode or magnet mode, in the presence of a magnetic field. In one example, control module 40 may detect a change in the characteristic of the EGM due to the MHD effect and transition operation of IMD 22 to the MRI mode in response to the detection. As described above, large static magnetic fields, such as those produced by MRI device 16, may interact with the blood of patient 12 as it flows through the magnetic field to produce a voltage. The magnitude of the induced voltage ($V_I$) may be determined in accordance with the equation:

$$V_I = B*v*d \sin \theta, \quad (1)$$

where B is the strength of the magnetic field, v is the velocity of flow of the blood, d is the diameter of the vessel through which the blood is flowing, and $\theta$ is the angle between the direction of the magnetic field and the direction of blood flow.

The voltages produced by the MHD effect may result in a change in a characteristic of an EGM sensed by IMD 22. For example, a voltage may be produced as the blood flows through the aortic arch upon being ejected from the left ventricle following electrical activation of the ventricle. Therefore, the MHD effect is observed subsequent to the R-wave or QRS complex. As such, the voltages produced by the MHD effect may result in a change in the S-T segment and/or the T-wave. In one instance, the voltage produced by the MHD effect may result in an increase in the amplitude of the T-wave, a change in a duration of the T-wave, a change in a frequency component of the T-wave, a change in morphology of the T-wave or another change in the T-wave. As such, control module 40 may monitor for such changes in the T-wave, e.g., by comparing T-wave amplitude changes to a threshold or performing template matching or wavelet analysis to detect morphology changes. In one example, control module 40 may determine the existence of the MHD effect when an amplitude of the T-wave changes by at least 50%. In another example, control module 40 may determine the existence of the MHD effect when the T-wave of the sensed EGM signal is compared with a T-wave of a template EGM signal (collected in the absence of a magnetic field) and has a correlation coefficient that is less than 0.7.

In another example, the voltage produced by the MHD effect may result in a decrease in a duration or length of the S-T segment, a change in a frequency component of the S-T segment, a change in the morphology of the S-T segment or other change in the S-T segment. In this case, control module 40 may monitor for such changes in the S-T segment, e.g., by comparing S-T segment lengths to a threshold or performing template matching or wavelet analysis to detect a shape change in the S-T segment. In some examples, control module 40 may monitor for one particular one of these changes, all of these changes or any combination of these EGM changes that are indicative of the presence of a strong magnetic field. In one example, control module 40 may determine the existence of the MHD effect when a duration of the S-T segment changes by at least 50%. In another example, control module 40 may determine the existence of the MHD effect when the S-T segment of the sensed EGM signal is compared with an S-T segment of a template EGM signal (collected in the absence of a magnetic field) and has a correlation coefficient that is less than 0.7.

As described above, the voltage produced by the MHD effect typically occurs after the ventricular contraction and therefore should not have a large effect on the P-wave, R-wave or QRS complex of the EGM. As such, control module 40 may monitor for instances in which the change in the S-T segment and/or the T-wave segment of the EGM is accompanied by little or no change in the associated P-wave, R-wave or QRS complex. If the change in the S-T segment or T-wave segment is accompanied by a change in the P-wave, R-wave or QRS complex, the change may be due to other causes and not necessarily the MHD effect from a strong magnetic field. Control module 40 may therefore monitor for changes in the amplitude and morphology of the P-wave, R-wave or QRS complex and detect existence of a strong magnetic field when a change in the S-T segment or the T-wave segment exceeds the respective threshold and the change in P-wave, R-wave or QRS complex is less than a corresponding threshold. Alternatively, control module 40 may monitor for a change in the EGM by monitoring for a change in the ratio of P-wave/T-wave amplitudes or a ratio of R-wave/T-wave amplitudes.

In response to detecting a change in a characteristic of the EGM indicative of the presence of a strong magnetic field, control module 40 may transition to operation of IMD 22 in the MRI mode. In this manner, the change in the characteristic of the EGM due to the MHD effect may be used to detect the MRI device and transition to the MRI mode.

As indicated by equation (1) above, there is a linear relationship between the induced voltage and the strength of the magnetic field, i.e., the voltage induced by the magnetic field will increase linearly with the strength of the magnetic field. Therefore, the change in the EGM e.g., amplitude of the T-wave, may increase linearly with the strength of the magnetic field. For example, an MRI device having a static magnetic field of 1.5 Tesla may result in a change in the amplitude of T-wave that is smaller than the change in the amplitude of the T-wave caused by MRI device having a static magnetic field of 3.0 Tesla. Control module 40 may therefore differentiate between different types of MRI devices based on the amount of change or magnitude of the change in the EGM signal. Control module 40 may transition operation of IMD 22 to an MRI mode corresponding with a type of MRI device 16. In other words, IMD 22 may have multiple MRI modes that each correspond with a particular type of MRI device and have different settings, e.g., different filter settings to filter out different frequencies. In some instances, implantable medical system 20 may only be approved for use with particular MRI devices. For example, implantable medical system 20 may be approved for use in a 1.5 Tesla MRI device. Thus, if a 3.0 T MRI device is detected, IMD 22 may generate an audible, visible or tactile alert notifying the patient or a telemetry alert to notify a technician or physician that IMD 22 is not approved for use in a 3.0 T MRI device.

In some instances, control module 40 may monitor for the MHD effect in conjunction with other criteria. In one embodiment, control module 40 may obtain the output of magnetic field sensor 46 and adjust operation of IMD 22 based on the output of magnetic field sensor 46 and the changes in the EGM signal. This may be useful when magnetic field sensor 46 is unable to differentiate between magnetic field strengths. For example, magnetic field sensor 46 may capable of determining whether a magnetic field exceeds a threshold, but not be capable of differentiating between two magnetic fields of different strength that both exceed the threshold. In other words, magnetic field sensor 46 may be a single threshold sensor that indicates whether a magnetic field exceeds a threshold (e.g., 1 mT). In this case, however, the single threshold sensor is not capable of differentiating between a 10-100 mT magnetic field (which may be the strength of a handheld magnet) and a 3.0 T magnetic field (which may be the strength of the static field of an MRI device 16). IMD 22 may therefore be unable to determine whether the magnetic field is from a handheld magnet (in which case the control processor should transition to the magnet mode) or is from a static magnetic field associated with MRI device 16 (in which case the control processor should transition to the MRI mode).

Control module 40 may analyze the EGM signal in addition to the output of the magnetic field sensor to differentiate between magnetic fields that exceed the threshold of magnetic field sensor 46. As described above, the magnetic field generated by handheld magnet does not produce much, if any, voltage caused by the MHD effect. To the extent a voltage is produced due to the MHD effect during application of handheld magnet, the induced voltage is small enough and far enough away from sensing electrodes of leads 24 to not change the characteristics of the EGM. On the other hand, the static magnetic field generated by MRI device 16 is larger in both strength and area of application. The voltages induced by the MHD effect from the static magnetic field of MRI device 16 are much larger than those induced by handheld magnet and may result in changes to the EGM. As such, control module 40 may determine that the magnetic field is associated with an MRI device 16 when the strength of the magnetic field exceeds the threshold of magnetic field sensor 46 and control module 40 detects the changes in the EGM corresponding with the MHD effect (e.g., changes in the S-T segment or T-wave in conjunction with relatively no change in the P-wave, R-wave or QRS complex). In this case, control module 40 may transition operation of IMD 22 to the MRI mode. Control module 40 may determine that the magnetic field is associated with handheld magnet when the strength of the magnetic field exceeds the threshold of magnetic field sensor 46 and control module 40 does not detect changes in the EGM corresponding with the MHD effect. In this case, control module 40 may transition operation of IMD 22 to the magnet mode. As such, monitoring for a change in the EGM due the MHD effect alone or in combination with a magnetic field sensor or other sensor, provides an effective way to differentiate magnetic fields of varying strengths. In one example, control module 40 may begin analyzing the EGM signal for the MDH effect in response to the magnetic field sensor 46 detecting presence of a magnetic field above the threshold, thereby reserving processing resources and power. In other examples, control module 40 may continuously be monitoring for changes in the EGM signal whether or not magnetic field sensor 46 detects presence of a magnetic field above the threshold.

As indicated in equation (1) above, the induced voltage is also related to the angle between the direction of the magnetic field and the direction of flow, i.e., the closer the blood flow is to being perpendicular to the direction of the magnetic field, the larger the induced voltage. A large induced voltage occurs when the blood is flowing through the aortic arch of the heart of patient 12, which is both larger in diameter than most of the other vasculature of the heart and because the aortic arch is more perpendicular to the direction of the magnetic field than other vasculature of the heart. Sensing the voltage induced by the MHD effect on the blood flowing through the aortic arch may be better sensed using certain sensing vectors. For example, a unipolar sensing vector may better sense the induced voltage than a bipolar sensing vector. As another example, sensing vector between an SVC coil and an RV coil of a defibrillation lead may be better than a bipolar sensing vector. To this end, control module 40 may reconfigure a sensing vector that is analyzed to monitor for a change in a characteristic of the EGM signal in response to magnetic field sensor 46 detecting a magnetic field that exceeds the threshold of magnetic field sensor 46. In one example, control module 40 may change the sensing vector from a bipolar sensing vector (e.g., tip-to-ring) to a unipolar sensing vector (e.g., tip-to-can, ring-to-can or coil-to-can) or to a SVC-to-RV sensing vector to monitor for the change to the EGM signal from the MHD effect.

After the MRI procedure is complete, control module 40 may transition operation of IMD 22 back to the normal mode of operation, e.g., turn high voltage therapy back on and/or have pacing that is triggered and/or inhibited as a function of sensed signals. Control module 40 may automatically revert to the normal mode of operation in response to magnetic field sensor 46 no longer detecting presence of the magnetic field, control module 40 no longer detecting the MHD effect on the EGM signal, after expiration of a timer or a combination thereof. Alternatively, control module 40 may transition operation of IMD 22 back to the normal mode in response to a command received from external device 34, such as programming device.

Figure 4:
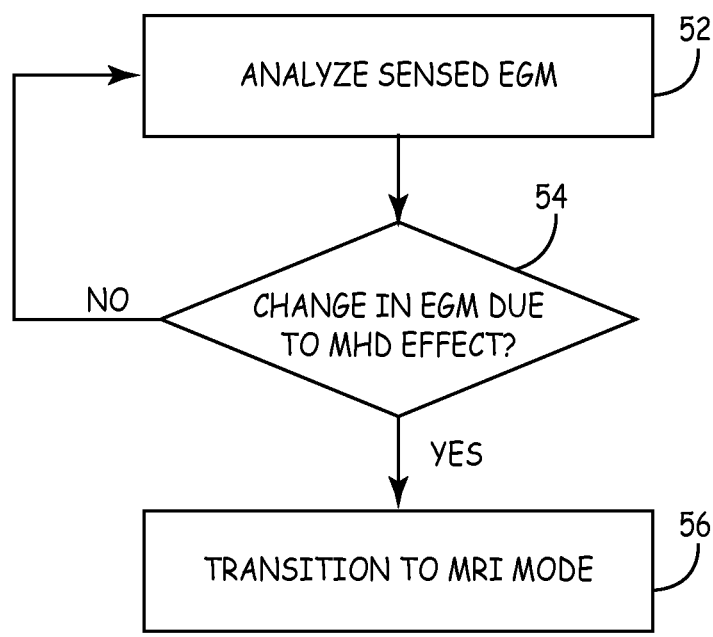
FIG. 4 is a flow diagram illustrating example operation of an implantable medical device detecting presence of a magnetic field based on a change in a characteristic of an EGM signal.

FIG. 4 is a flow diagram illustrating example operation of an implantable medical device to detect presence of a magnetic field based on a change in a characteristic of an EGM signal. Control module 40 of IMD 22 analyzes a sensed EGM signal (52). Control module 40 determines whether a characteristic of the EGM signal is indicative of the presence of a strong magnetic field (54). As described above, the strong magnetic field may induce a voltage due to the MHD effect that may change a characteristic of the EGM signal. The voltage produced by the MHD effect may result in a change in the S-T segment and/or the T-wave of the EGM signal. In one example, the voltage produced by the MHD effect may result in an increase in the amplitude of the T-wave, a change in morphology of the T-wave or another change in the T-wave. In another example, the voltage produced by the MHD effect may result in a decrease in the length of the S-T segment, a change in the shape of the S-T segment or other change in the S-T segment. In some instances, the change to the S-T segment or T-wave of the EGM must be accompanied by relatively little or no change in the P-wave, R-wave or QRS complex of the EGM.

In response to detecting a change in a characteristic of the EGM ("YES" branch of block 54), control module 40 may transition operation of IMD 22 to an MRI mode (56). In this manner, the change in the characteristic of the EGM due to the MHD effect may be used to detect the MRI device and transition to the MRI mode. In response to not detecting a change in a characteristic of the EGM signal ("NO" branch of block 54), control module continues to analyze subsequent EGM signals.

Figure 5:
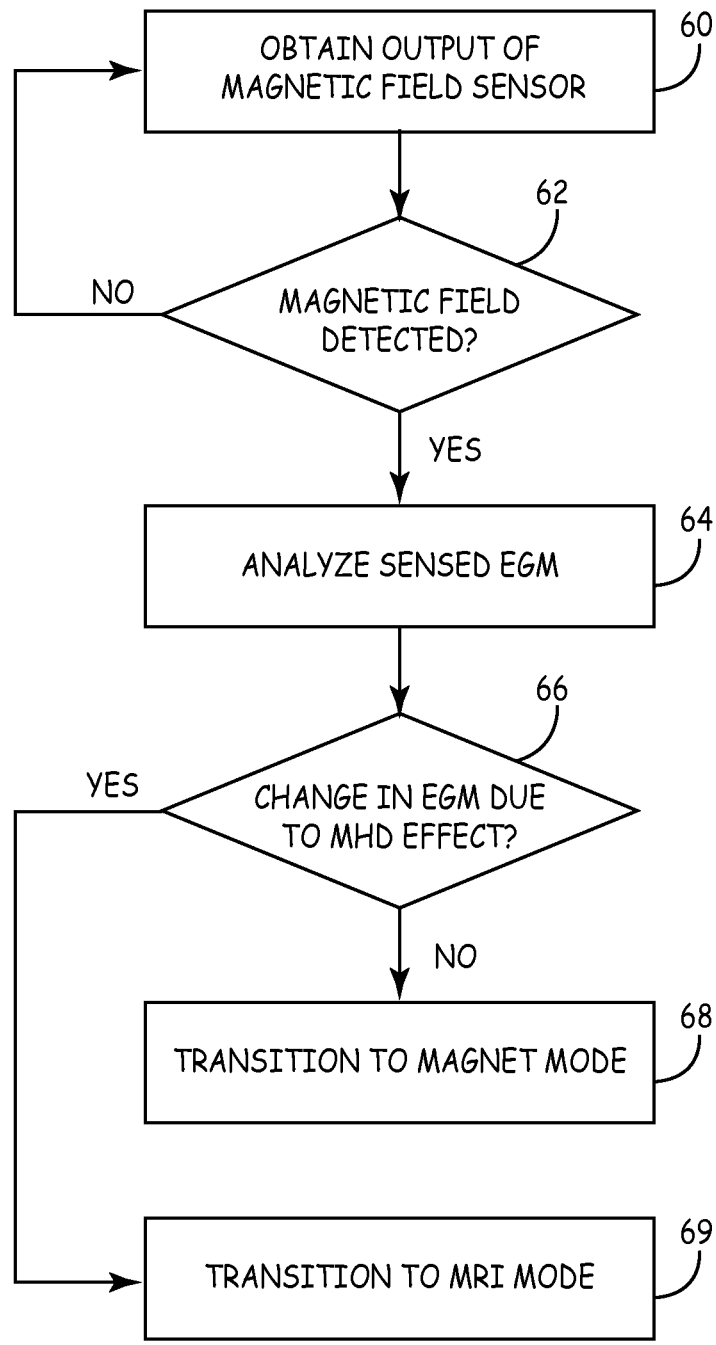
FIG. 5 is a flow diagram illustrating example operation of an implantable medical device distinguishing between different types of magnetic fields based on a change in a characteristic of an EGM signal.

FIG. 5 is a flow diagram illustrating example operation of an implantable medical device distinguishing between different types of magnetic fields based on a change in a characteristic of an EGM signal. Control module 40 obtains output of magnetic field sensor 46 (60). Control module 40 determines whether a magnetic field is detected based on the output of the magnetic field sensor 46 (62). Magnetic field sensor 46 may, for example, output a first value when a magnetic field within the vicinity of IMD 22 does not exceed a threshold (e.g., 1 mT) and output a second value when a magnetic field within the vicinity of IMD 22 exceeds the threshold. Control module 40 may detect a magnetic field when the output of magnetic field sensor 46 is the second value.

When control module 40 does not detect a magnetic field ("NO" branch of block 62), control module 40 continues to obtain the output of magnetic field sensor 46. When control module 40 does detect a magnetic field ("YES" branch of block 62), control module 40 analyzes a sensed EGM signal (64). Control module 40 determines whether a characteristic of the EGM signal indicative of the presence of a strong magnetic field exists (66). As described above, control module 40 may analyze the EGM to monitor for a change in the S-T segment and/or the T-wave of the EGM signal indicative of the MHD effect caused by a strong magnetic field. In one example, the change to the S-T segment or T-wave of the EGM must be accompanied by relatively little or no change in the corresponding P-wave, R-wave or QRS complex of the EGM.

In response to not detecting a change in a characteristic of the EGM signal ("NO" branch of block 66), control module 40 transitions operation of IMD 22 to a magnet mode (68). In response to detecting a change in a characteristic of the EGM ("YES" branch of block 66), control module 40 transitions operation of IMD 22 to an MRI mode (70). In this manner, the change in the characteristic of the EGM due to the MHD effect may be used to differentiate between magnetic fields produced by different sources, e.g., differentiate a magnetic field produced by a handheld magnet (which may be between 100 mT) from a magnetic field produced by an MRI device 16 (which may be greater than 1 T).

Figure 6:
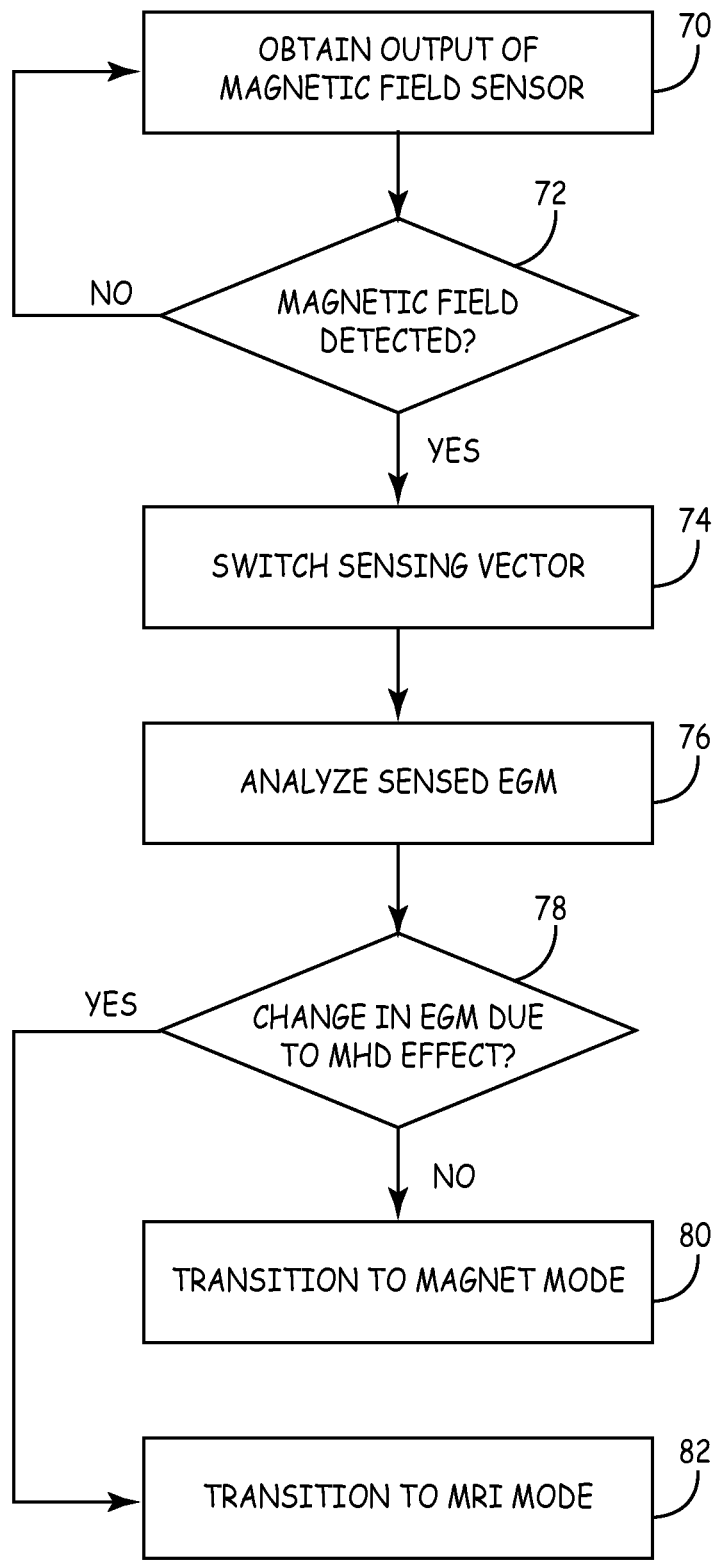
FIG. 6 is a flow diagram illustrating another example operation of an implantable medical device distinguishing between different types of magnetic fields based on a change in a characteristic of an EGM signal.

FIG. 6 is a flow diagram illustrating another example operation of an implantable medical device distinguishing between different types of magnetic fields based on a change in a characteristic of an EGM signal. Control module 40 obtains output of magnetic field sensor 46 (70). Control module 40 determines whether a magnetic field is detected based on the output of the magnetic field sensor 46 (72). Magnetic field sensor 46 may, for example, output a first value when a magnetic field within the vicinity of IMD 22 does not exceed a threshold (e.g., 1 mT) and output a second value when a magnetic field within the vicinity of IMD 22 exceeds the threshold. Control module 40 may detect a magnetic field when the output of magnetic field sensor 46 is the second value.

When control module 40 does not detect a magnetic field ("NO" branch of block 72), control module 40 continues to obtain the output of magnetic field sensor 46. When control module 40 does detect a magnetic field ("YES" branch of block 72), control module 40 switches a sensing vector of IMD 22 (74) Sensing the voltage induced by the MHD effect on the blood flowing through specific heart chambers or blood vessels (e.g., the aortic arch) may be better sensed using certain sensing vectors. For example, a unipolar sensing vector may better sense the induced voltage than a bipolar sensing vector. As another example, a sensing vector between an SVC coil and an RV coil of a defibrillation lead may be better than a bipolar sensing vector. In one example, control module 40 may change the sensing vector from a bipolar sensing vector (e.g., tip-to-ring or tip-to-RV coil) to a unipolar sensing vector (e.g., tip-to-can, ring-to-can, coil-to-can or tip-to-SVC coil) or to a SVC coil-to-RV coil sensing vector to monitor for the change to the EGM signal from the MHD effect. In this manner, the sensing vector may be optimized for sensing an EGM with a more prominent change in the characteristic of the EGM due to the MHD effect.

Control module 40 analyzes the EGM signal sensed using the adjusted sensing vector (76). Control module 40 determines whether a characteristic of the EGM signal indicative of the presence of a strong magnetic field exists (78). As described above, control module 40 may analyze the EGM to monitor for a change in the S-T segment and/or the T-wave of the EGM signal indicative of the MHD effect caused by a strong magnetic field. In one example, the change to the S-T segment or T-wave of the EGM must be accompanied by relatively little or no change in the corresponding P-wave, R-wave or QRS complex of the EGM.

In response to not detecting a change in a characteristic of the EGM signal ("NO" branch of block 78), control module 40 transitions operation of IMD 22 to a magnet mode (80). In response to detecting a change in a characteristic of the EGM ("YES" branch of block 78), control module 40 transitions operation of IMD 22 to an MRI mode (82). Thus, the change in the characteristic of the EGM due to the MHD effect may be used to differentiate between magnetic fields produced by different sources.

Figure 7:
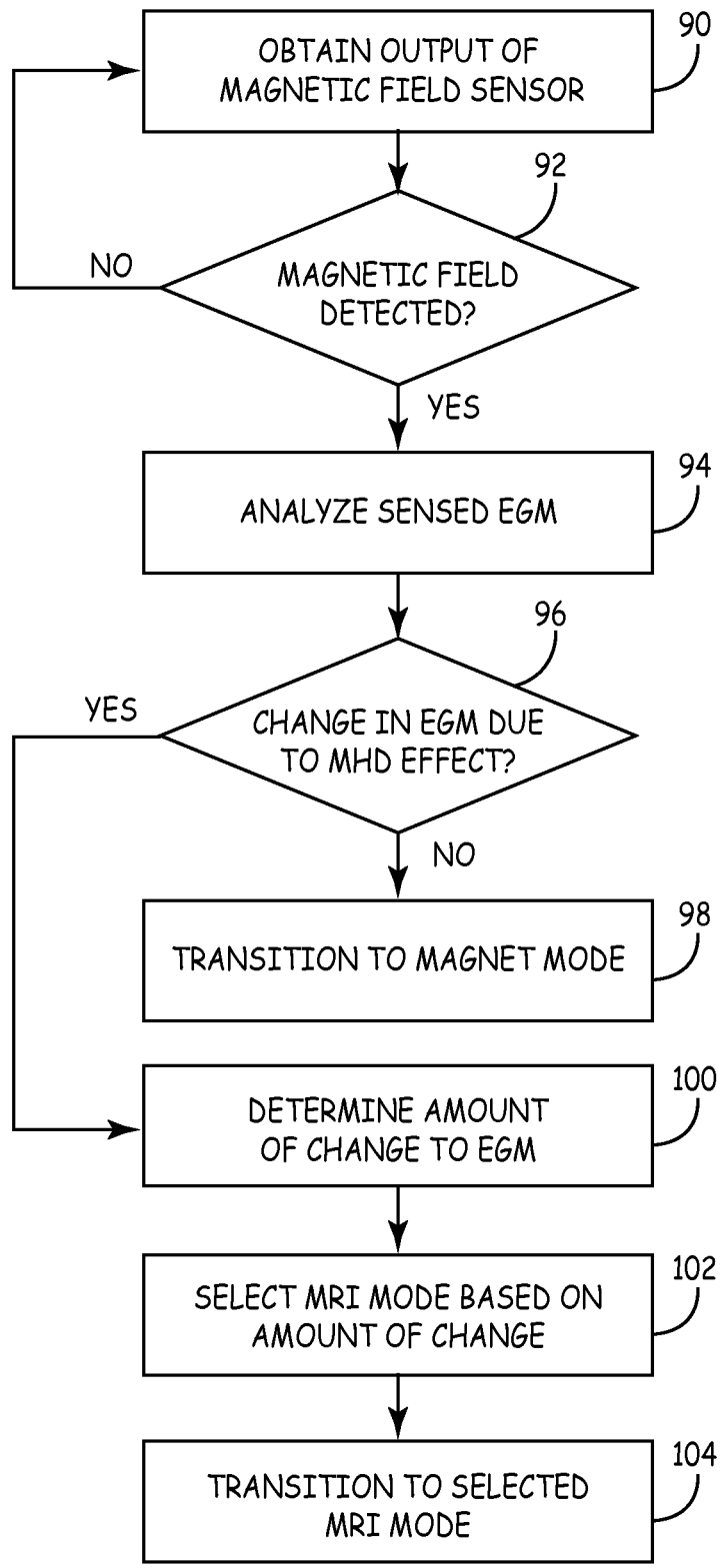
FIG. 7 is a flow diagram illustrating another example operation of an implantable medical device distinguishing between different types of magnetic fields based on a change in a characteristic of an EGM signal.

FIG. 7 is a flow diagram illustrating another example operation of an implantable medical device distinguishing between different types of magnetic fields based on a change in a characteristic of an EGM signal. Control module 40 obtains output of magnetic field sensor 46 (90). Control module 40 determines whether a magnetic field is detected based on the output of the magnetic field sensor 46 (92). Magnetic field sensor 46 may, for example, output a first value when a magnetic field within the vicinity of IMD 22 does not exceed a threshold (e.g., 1 mT) and output a second value when a magnetic field within the vicinity of IMD 22 exceeds the threshold. Control module 40 may detect a magnetic field when the output of magnetic field sensor 46 is the second value.

When control module 40 does not detect a magnetic field ("NO" branch of block 92), control module 40 continues to obtain the output of magnetic field sensor 46. When control module 40 does detect a magnetic field ("YES" branch of block 92), control module 40 analyzes a sensed EGM signal (94). Control module 40 determines whether a characteristic of the EGM signal indicative of the presence of a strong magnetic field exists (96). As described above, control module 40 may analyze the EGM to monitor for a change in the S-T segment and/or the T-wave of the EGM signal indicative of the MHD effect caused by a strong magnetic field. In one example, the change to the S-T segment or T-wave of the EGM must be accompanied by relatively little or no change in the corresponding P-wave, R-wave or QRS complex of the EGM.

In response to not detecting a change in a characteristic of the EGM signal ("NO" branch of block 96), control module 40 transitions operation of IMD 22 to a magnet mode (98). In response to detecting a change in a characteristic of the EGM ("YES" branch of block 96), control module 40 determines a magnitude of the change of the characteristic of the EGM signal (100). As indicated by equation (1) above, there is a linear relationship between the induced voltage and the strength of the magnetic field, i.e., the voltage induced by the magnetic field will increase linearly with the strength of the magnetic field. Therefore, the change in the EGM signal, e.g., amplitude of the T-wave, may increase linearly with the strength of the magnetic field. For example, an MRI device having a static magnetic field of 1.5 Tesla may result in a change in the amplitude of T-wave that is smaller than the change in the amplitude of the T-wave caused by an MRI device having a static magnetic field of 3.0 Tesla. Control module 40 may therefore differentiate between different types of MRI devices based on the magnitude of the change in the EGM signal.

Control module 40 selects an MRI mode based on the magnitude of the change in the EGM signal (102). In other words, IMD 22 may have multiple MRI modes that each correspond with a particular type of MRI device. Control module 40 may select the MRI mode that corresponds with the magnitude of the change in the EGM signal, e.g., based on an amount that the amplitude of the T-wave increased. Control module 40 transitions operation of IMD 22 to the selected MRI mode (104). In this manner, the change in the characteristic of the EGM due to the MHD effect may be used to differentiate between magnetic fields produced by more than two different sources.

The techniques described herein may be applicable to other therapy systems. For example, the techniques described herein may be applicable to systems including an IMD that delivers electrical stimulation therapy to other muscles, nerves or organs of patient 12. As another example, the techniques described herein may be applicable to systems including an implantable drug delivery or infusion device or an IMD including a drug delivery or infusion module. Other combinations of implantable devices will be obvious to one of skill in the art, and fall within the scope of this disclosure.

The techniques described in this disclosure, including those attributed to IMD 22, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, or flash memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
    identifying a change in a characteristic of an electrogram (EGM) measured by an implantable medical device indicative of the presence of a static magnetic field, wherein the EGM corresponds to cardiac activity of a heart of a patient;
    determining a magnitude of the change in the characteristic of the EGM;
    detecting the presence of the static magnetic field based at least on the magnitude of the change in the characteristic of the EGM; and
    adjusting operation of the implantable medical device in response to detecting the presence of the static magnetic field.

2. The method of claim 1, wherein identifying the change in the characteristic of the EGM indicative of the presence of a magnetic field comprises identifying a change in a T-wave of the EGM.

3. The method of claim 2, wherein identifying the change in the T-wave comprises one of identifying a change in an amplitude of the T-wave, a change in a duration of the T-wave, a change in a frequency component of the T-wave, and a change in a morphology of the T-wave.

4. The method of claim 1, wherein identifying a change in a characteristic of the EGM indicative of the presence of a magnetic field comprises identifying a change in a T-wave of the EGM in which at least one of the corresponding P-wave, R-wave and QRS complex is substantially unchanged.

5. The method of claim 1, wherein identifying the change in the characteristic of the EGM comprises identifying a change in an S-T segment of the EGM.

6. The method of claim 5, wherein identifying the change in the S-T segment of the EGM further comprises identifying the change in a duration of the S-T segment, a change in a frequency component of the S-T segment, and a change in a morphology of the S-T segment.

7. The method of claim 1, wherein identifying the change in the characteristic of the EGM comprises identifying a change in a ratio of an amplitude of one of an R-wave and a P-wave and an amplitude of a corresponding T-wave.

8. The method of claim 1, wherein adjusting operation of the implantable medical device comprises transitioning from a first operating mode to a second operating mode.

9. The method of claim 8, wherein the second operating mode comprises one of a magnet mode and a magnetic resonance imaging (MRI) mode.

10. An implantable medical system comprising:
at least one implantable medical lead that includes at least one electrode; and
an implantable medical device connected to the medical lead, the implantable medical device comprising a control module configured to identify a change in a characteristic of an electrogram (EGM) indicative of the presence of a static magnetic field, determine a magnitude of the change in the characteristic of the EGM, detect the presence of the static magnetic field based at least on the magnitude of the change in the characteristic of the EGM, and adjust operation of the implantable medical device in response to detecting the presence of the static magnetic field,
wherein the EGM corresponds to cardiac activity of a heart of a patient.

11. The system of claim 10, wherein the control module identifies a change in a T-wave of the EGM indicative of the presence of a magnetic field.

12. The system of claim 11, wherein the control unit identifies one of a change in an amplitude of the T-wave of the EGM, a change in a duration of the T-wave, a change in a frequency component of the T-wave, and a change in a morphology of the T-wave of the EGM indicative of the presence of a magnetic field.

13. The system of claim 10, wherein the control unit identifies a change in a T-wave of the EGM that corresponds with one of a P-wave, R-wave and QRS complex that is substantially unchanged.

14. The system of claim 10, wherein the control module identifies a change in an S-T segment of the EGM indicative of the presence of a magnetic field.

15. The system of claim 14, wherein the control module identifies a change in at least one of a duration of the S-T segment, a change in a frequency component of the S-T segment, and a change in a morphology of the S-T segment indicative of the presence of a magnetic field.

16. The system of claim 10, wherein the control module identifies a change in the EGM indicative of the presence of a magnetic field upon identifying a change in a ratio of an amplitude of one of an R-wave and a P-wave and an amplitude of a corresponding T-wave.

17. The system of claim 10, wherein adjusting operation of the implantable medical device comprises transitioning from a first operating mode to a second operating mode.

18. The system of claim 10, wherein the second operating mode comprises one of a magnet mode and a magnetic resonance imaging (MRI) mode.

19. A computer-readable medium comprising instructions that, when executed, cause an implantable medical device to:
identify a change in a characteristic of an electrogram (EGM) indicative of the presence of a static magnetic field, wherein the EGM corresponds to cardiac activity of a heart of a patient;
determine a magnitude of the change in the characteristic of the EGM;
detect the presence of the static magnetic field based at least on the magnitude of the change in the characteristic of the EGM; and
adjust operation of the implantable medical device in response to detecting the presence of the static magnetic field.

* * * * *